United States Patent [19]

White et al.

[11] 4,160,802

[45] Jul. 10, 1979

[54] INSTRUMENT FOR THE AUTOMATED DETERMINATION OF ORGANIC HALOGENS

[75] Inventors: Robert H. White, Houston, Tex.; Lowell P. Hager, Urbana, Ill.

[73] Assignee: University of Illinois Foundation, Urbana, Ill.

[21] Appl. No.: 880,372

[22] Filed: Feb. 23, 1978

[51] Int. Cl.² ............... G01N 31/06; G01N 31/12; G01N 31/22

[52] U.S. Cl. .................................. 422/68; 422/78; 422/57; 23/230 PC

[58] Field of Search ........ 23/253 R, 253 TP, 253 PC; 422/68, 78, 57

[56] References Cited

U.S. PATENT DOCUMENTS

| | | | |
|---|---|---|---|
| 810,870 | 1/1906 | Kirkwood | 23/253 PC |
| 3,141,741 | 7/1964 | Hoel et al. | 23/253 PC |
| 3,298,785 | 1/1967 | Ruel | 23/253 PC |
| 4,070,155 | 1/1978 | Fraim | 23/253 PC |

OTHER PUBLICATIONS

Automation in Analytical Chemistry, Technicon Symposia 1967, vol. I; Vernot et al., pp. 423–426.
White et al., A Method for the Rapid Determination of Trace Organic Halogens in Lipids Analytical Biochem, 78, 52–56 (1977).
Treatise on Analyt. Chem., Halogens Part II, vol. 7, pp. 353–391.

Primary Examiner—Michael S. Marcus
Attorney, Agent, or Firm—Mathew L. Kalinowski

[57] ABSTRACT

A rapid, automated method for the determination of organic halogens is provided by an analytical system comprising a burner and combustion chamber for burning the organic halogen-containing sample in an oxygen-hydrogen flame; an absorption zone wherein the combustion gases are absorbed in a moving reagent film; and a colorimeter and recorder. With proper choice of reagent film, either total halogen (Cl, Br, I) content or specifically bromine content can be assayed automatically. The system is particularly useful for analysis of biological samples.

5 Claims, 2 Drawing Figures

INSTRUMENT FOR THE AUTOMATED DETERMINATION OF ORGANIC HALOGENS

The invention described herein was made in the course of work supported by the National Science Foundation.

This invention relates to a novel automated analytical system for the determination of organic halogen content (Cl, Br, I). In a specific embodiment, this invention relates to an analytical instrument comprising a burner and combustion zone for burning the organic halogen-containing sample in an oxygen-hydrogen flame; an absorption zone wherein the combustion gases are absorbed in a moving reagent film; and a colorimeter and recorder for automated assay of halogen content. The instrument is particularly suited to the rapid determination of trace lipid-soluble organic halogenated compounds in biological materials.

A large number of methods exist in the prior art for the quantitative determination of halogens in organic compounds. These methods are reviewed in detail in *Treatise on Analytical Chemistry*, Part II, Vol. 7, p. 335, John Wiley & Sons, Inc., New York, 1969; and *Treatise on Analytical Chemistry*, Part II, Vol. 14, p. 1, John Wiley & Sons, Inc., New York, 1971; which citations are incorporated herein by reference as illustrative of the state of the art.

Most prior art methods require first the conversion of organic halogen to the halide ion, and second, the quantitative determination of the halide ion produced. The halide ion is conventionally determined by reaction with silver ion, for example in gravimetric, titrimetric, or nephelometric procedures.

Among the prior art methods for converting organic halogen to halide ion are the Carius combustion, Pregl combustion, and sodium peroxide bomb procedures. The Carius method involves heating the sample with fuming nitric acid and silver nitrate in a sealed tube to produce silver halide. Pregl combustion involves oxidizing the sample over a platinum wire to produce free halogen which is then reduced with bisulfite or hydrazine to halide ion. In the sodium peroxide procedure, the sample is converted to sodium halide which can then be determined by reaction with silver ion. All of the above-listed methods involve handling the sample in several steps and are time consuming.

The above-mentioned and other disadvantages of prior art methods can be overcome by utilizing the automated instrument of this invention. The instrument comprises, in series arrangement, a combustion chamber for burning an organic halogen-containing sample in an oxygen-hydrogen flame; a burner for introducing and atomizing the sample in a rapid flow of hydrogen gas and for supplying oxygen to the atomized sample for combustion; an absorption zone including a supported moving liquid film for absorption of the hydrogen halides produced by combustion, said film comprising a colorimetric reagent solution; a solution zone wherein the reagent solution containing absorbed halogen halides is collected and wherein inert gases are vented; a colorimeter and recorder to monitor and record the halogen content; and a pump for transferring the reagent solution from storage vessels and for establishing the moving film in the absorption zone.

The burner is of novel construction and includes a metal or glass cylindrical body; a fixed needle along the axis of the cylindrical body for introducing the sample, the needle extending to an atomizing zone wherein a rapid hydrogen flow atomizes the sample; a first orifice in the cylindrical body providing for flow of the atomized sample from the atomizing zone to the combustion chamber; a plurality of orifices surrounding the first orifice providing for flow of oxygen-containing gas for burning the atomized sample; and means for external cooling of the burner. With proper choice of reagent solutions, the instrument is readily adapted to rapid determination of either total halogen content or, specifically, bromine content.

The construction and operation of the instrument of this invention are further illustrated by reference to the drawings and description of the preferred embodiments:

Figure 1:
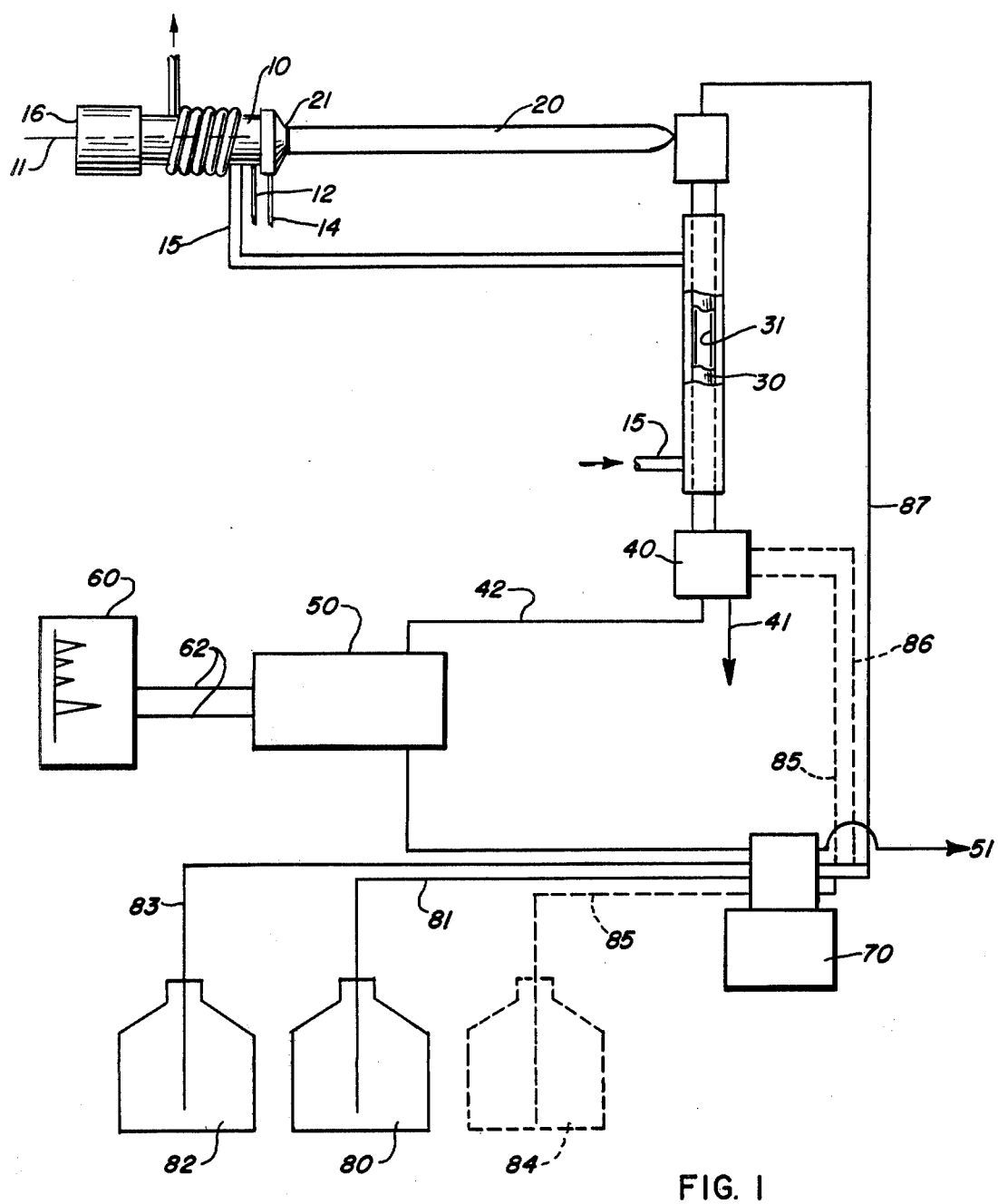
FIG. 1 illustrates the elements comprising the instrument of this invention.
Figure 2:
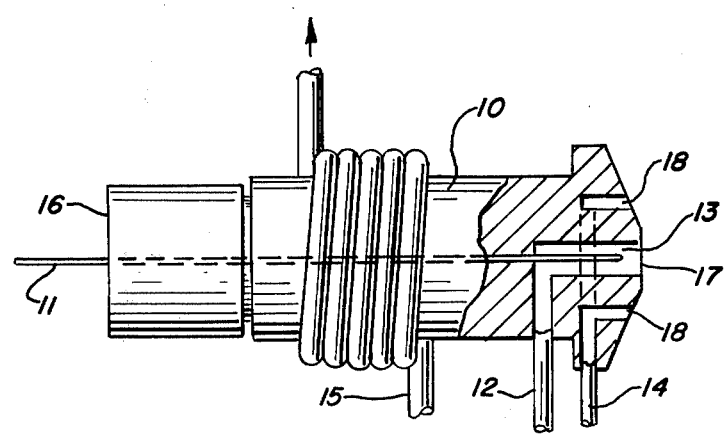
FIG. 2 illustrates in detail the design of the burner.

To determine total organic halogen content, the sample is advantageously dissolved in a solvent such as toluene or benzene. From 4–10 $\mu l$ of this solution is injected manually into burner 10 by way of syringe needle 11, suitably a 0.021 inch, blunt tipped Hamilton 10 $\mu l$ syringe needle, extending from septum 16 to atomizing zone 13. The sample is atomized in zone 13 with a flow of hydrogen of about 0.5 liters per minute introduced via inlet 12. The atomized sample flows from orifice 17 (0.024 inches) and is mixed with oxygen flowing at a rate of about 1.5 liters per minute from orifices 18 via inlet 14. Advantageously, six such orifices, each 0.025 inches in diameter, are arranged in hexagonal pattern about orifice 17. The burner body is made of glass or of metal such as stainless steel, and is about 1–2" long and about ½" in diameter.

The sample is then burned in combustion chamber 20 which suitably is a quartz tube about 17 cm long and is joined to the burner with asbestos seal 21. Water-soluble combustion gases (HCl, HBr, and HI) are absorbed in moving reagent film 31 within absorption zone 30, which can be a 20 cm glass condensor. The reagent film is produced by mixing two solutions just prior to use in line 87. The first solution stored in vessel 82, is transferred to absorption zone 30 via lines 87 and 83, and contains 200 ml saturated solution of mercuric thiocyanate in ethanol and 1 liter of water containing 0.1 g sodium dodecylsulfate.

The second solution stored in vessel 80, is transferred to line 87 via line 81, and contains 200 ml of a solution of 0.37 M ferric nitrate and 5.25 M perchloric acid and 1 liter of water. Each of these solutions is pumped by peristaltic pump 70 at about 0.78 ml per minute.

The reagent solution containing absorbed combustion gases is collected in collector zone 40 where inert gases are vented via line 41. The reagent solution is then transferred via line 42 to colorimeter 50. The presence of halogens is indicated by the formation of red iron thiocyanate color which is monitored at 450 nm by the colorimeter and is recorded on recorder 60 connected to the colorimeter via lines 62. Reagent solution is removed from the colorimeter and discarded via line 51. In operation, burner 10 and absorption zone 30 are cooled by water circulating in line 15. To prevent water condensation, the quartz combustion is kept well above the boiling point of water during the operation.

The instrument of this invention is readily adapted to the specific determination of bromine content. For this purpose, the bromide produced in the flame is oxidized to bromine with chloramine-T which is then reacted with phenol red (phenolsulfonphthalein) at pH 4.6. This reaction produces tetrabromophenol red which is monitored colorimetrically at 589 nm. Specifically, the hydrogen bromide produced in combustion zone 20 is absorbed in moving reagent film 31. The reagent film solution stored in vessel 80, is transferred to absorption zone 30 via line 81 and line 87, and contains 0.1 N sodium acetate buffer (pH 4.6) and 0.1 g sodium dodecylsulfate per liter. After collection of the sample in zone 40, the bromide is oxidized to bromine by addition of $2.5 \times 10^{-3}$ M chloramine-T solution, which is stored in vessel 82 and transferred via line 83 and line 86 to zone 40. The bromine is then converted to tetrabromophenol red by reaction with phenol red solution (8 mg per liter) which solution is stored in vessel 84 and is transferred to zone 40 via line 85. Peristaltic pump 70 pumps the sodium acetate buffer at 20 ml per minute; the chloramine-T solution at 0.6 ml per minute; and the phenol red solution at 0.1 ml per minute. The tetrabromophenol red is monitored at 589 nm in colorimeter 50 and recorded in recorder 60.

Standard curves were generated by injecting known amounts of organic compounds in suitable solvents, for example, solutions of known concentrations of 2-chloro-5nitrobenzoic acid in toluene. A new standard curve was generated each time a set of unknown samples was run. Standard curves were generated in similar manner with organic bromine compounds using either the total halogen-specific system or the bromine-specific system.

Owing to the design of the instrument, the peak shapes and, thus, their heights are a function of the volume of sample injected, the rate at which the sample is injected, and the content of organic halogen. Errors due to variations in the volume injected were eliminated by using the same volume of solvent for generating the standard curves and assaying the unknowns. Repeated analyses of 10 $\mu$l samples containing 0.6 $\mu$g of organic chlorine by an experienced operator, taking care to inject each at the same rate, give a series of peaks the heights of which would not vary by more than ±5%. Analyses of toluene solutions of several chloro and bromo compounds containing equivalent amounts of halogen were within ±10%.

The instrument is particularly suited to analysis of biological samples such as the halogenated, lipid soluble, organic compounds in marine organisms. Over 600 different species of marine organisms have been assayed by the methods described. An average lipid organic chlorine content of 11.9 $\mu$g/g wet weight of tissue was found. The average value for bromine was 8.3 $\mu$g/g. In these assays, the instrument's performance proved it to be both sensitive and reliable. This, coupled with its speed of analysis (~15 sec/sample), makes it a very useful device for the rapid determination of trace halogenated organic compounds, especially when a large number of samples is to be assayed.

Although this invention has been disclosed in detail with particular reference to certain preferred embodiments thereof, it is understood that variations and modifications can be effected within the spirit and scope of the appended claims. It is intended that all material contained in the above descriptions and figures shall be interpreted in an illustrative and not in a limiting sense.

What is claimed is:

1. An instrument for the automated determination of organic halogen content comprising in series arrangement:
   (a) an elongated combustion chamber, having an inlet end and an outlet end, for burning an organic halogen-containing sample in an oxygen-hydrogen flame;
   (b) a burner, affixed via a seal to the inlet end of the combustion chamber, having means for introducing and atomizing the sample in a rapid flow of hydrogen gas, and means for supplying oxygen to the atomized sample for combustion;
   (c) absorption means, affixed to the outlet end of the combustion chamber, including means for forming a supported moving film for absorbing the halogen-containing combustion gases, said film comprising a colorimetric reagent solution;
   (d) means for collecting the halogen-containing reagent solution and venting therefrom inert, water-insoluble gases;
   (e) colorimeter means, connected to the collection means, for receiving and monitoring the halogen content of the vented reagent solution; and
   (f) pump means for transferring the reagent solution from storage vessels and establishing the moving liquid film.

2. The instrument of claim 1 wherein the burner comprises:
   (a) a cylindrical body;
   (b) a fixed needle along the axis of the cylindrical body for introducing the sample, said needle extending to an atomizing zone wherein a rapid hydrogen flow atomizes the sample;
   (c) a first orifice in the cylindrical body providing for flow of the atomized sample from the atomizing zone to the combustion chamber;
   (d) a plurality of orifices surrounding said first orifice providing for flow of oxygen-containing gas for admixture with and combustion of the atomized sample in the combustion zone; and
   (e) means for external cooling of the burner.

3. The instrument of claim 1 wherein the absorption means includes:
   (a) a tubular body, the inner wall of which provides support for said moving liquid film; and
   (b) means for external cooling of the tubular body.

4. The instrument of claim 1 wherein the pump means include a peristaltic pump.

5. The instrument of claim 1 wherein the combustion chamber is a quartz tube and the seal is an asbestos seal.

* * * * *